United States Patent

Blasingame et al.

[11] Patent Number: 5,810,832
[45] Date of Patent: Sep. 22, 1998

[54] INSTRUMENT FOR PLACEMENT OF CERCLAGE WIRE

[76] Inventors: James Blasingame, 694 Rimine Rd., Del Mar, Calif. 92014; Stephen C. Shoemaker, 4975 Lakewood Ct., San Diego, Calif. 92122

[21] Appl. No.: 773,606

[22] Filed: Dec. 27, 1996

[51] Int. Cl.[6] ................................................. A61B 17/58
[52] U.S. Cl. .............................. 606/103; 606/74; 606/139
[58] Field of Search .............................. 606/103, 74, 139, 606/148, 144, 140

[56] References Cited

U.S. PATENT DOCUMENTS

| | | | |
|---|---|---|---|
| 4,146,022 | 3/1979 | Johnson et al. | 128/92 B |
| 4,587,963 | 5/1986 | Leibinger et al. | 128/92 B |
| 4,606,335 | 8/1986 | Wedeen | 128/92 E |
| 4,622,960 | 11/1986 | Tam | 128/92 VK |
| 4,667,662 | 5/1987 | Titone et al. | 128/92 YD |
| 5,116,340 | 5/1992 | Songer et al. | 606/74 |
| 5,447,512 | 9/1995 | Wilson et al. | 606/139 |
| 5,501,688 | 3/1996 | Whiteside et al. | 606/103 |
| 5,573,542 | 11/1996 | Stevens | 606/139 |
| 5,601,572 | 2/1997 | Middleman et al. | 606/139 |

OTHER PUBLICATIONS

*Operative Orthopaedics*, vol. 1, Edited by Michael W. Chapman, M.D., 1988, Chapter 12, "Principles of Wire Fixation", D.H. Gershuni, pp. 141–149.

*AO/ASIF Instruments and Implants: A Technical Manual*, F. Baumgart, J. Buchanan, J.A. Disegi, R. Hertel, A. Murphy, S.M. Perren, 1981, pp. 9–29; 362–369.

*Primary Examiner*—Michael Buiz
*Assistant Examiner*—Julian W. Woo
*Attorney, Agent, or Firm*—Brown, Martin, Haller & McClain

[57] ABSTRACT

The cerclage instrument comprises a hollow housing having a handgrip at its proximal end for gripping in the user's hand to support and control movement of the device. At the distal end of the housing is a tapered tip with an opening therein. Disposed slidably within the housing is an extendable tongue formed from spring metal or similar material that will coil or curl to form a loop when extended outside of the housing. At its distal end, the tongue has an eyelet or notch for retaining the end of a cerclage wire so that it can be pulled around the bone. At its proximal end, the tongue is attached to a plunger or slide within the housing which permits the tongue to be extended from and retracted into the housing. The curvature of the tongue when extended causes it to closely follow the circumference of the bone during extension and retraction.

20 Claims, 3 Drawing Sheets

INSTRUMENT FOR PLACEMENT OF CERCLAGE WIRE

BACKGROUND OF THE INVENTION

1. Field of the Invention

The present invention relates to an instrument for passing cerclage wire around a bone for fixation of a fracture and more particularly to a cerclage instrument having a flexible means for closely following the circumference of the bone to minimize soft tissue trauma.

2. Description of Related Art

Numerous tools and techniques are used by orthopedic surgeons for internal fixation of bone fractures, including placement of plates, screws, pins, nails and wires. The choice of fixation method depends on the nature and location of the fracture, and may involve the use of multiple fixation devices for temporary or definitive fixation. Cerciage wiring techniques are frequently used following reduction for provisional fixation of long bone fractures to stabilize the bone for placement of screws, nails or rods, after which the wires are removed. They may also be used for definitive fixation in combination with other fixation devices.

Cerclage wires are passed around the bone shaft perpendicular to the long axis of the bone using a "wire passer", which is an instrument having a shaft with a curved end and an eyelet or notch in the curved end for guiding the wire around the bone. Cerclage instruments are available in different curvature diameters, e.g., 70 mm and 45 mm, for use with larger or smaller diameter bones. The curved end of the instrument is positioned around the bone and the wire is inserted into the eyelet so that it can be pulled around the bone as the instrument is withdrawn. After the wire has encircled the bone, the ends are twisted using wire tighteners or forceps. Care must be taken during the cerclage procedure to avoid soft tissue trauma resulting from excessive exposure or stripping of musculature away from the bone.

A number of cerclage instruments, or wire passers, have been devised in recent years to facilitate the positioning and fixation of cerclage wire. For example, the patent of Wedeen (Pat. No. 4,606,335) describes a handle structure with an S-shaped portion which has an eyelet at the end for retaining the wire. The curvature of the S-portion allows the device to be inserted into the incision then manually rotated to partially encircle the bone, and is particularly suited for fractures of the femoral shaft, where the mass of the quadriceps musculature impairs motion of the passer handle and makes it difficult to bring the distal end of the passer into view. The Wedeen device still requires significant spreading of the incision and/or other soft tissue trauma in order to pass the device around the bone, rotate the curved tip, and have access to the eyelet in the tip once the tool has completed its travel around the bone.

The cerclage device disclosed by Whiteside, et al. (Pat. No. 5,501,688), looks something like a corkscrew having a hooked end for partially encircling the bone, and a handle assembly which provides a crank to twist the ends of the wires together to tighten the wire around the bone using the same instrument. The object of this particular device is to reduce the fatigue resulting from repeated placement and twisting of wires, which procedures involve the use of at least two different instruments. This device still has the problem of requiring significant spreading of the incision and muscle trauma in order to allow the tip of the device to completely travel around the bone so that the tip can be viewed for insertion of the wire into the eyelet.

While the cerclage devices in the prior art are designed with a curvature to partially encircle the bone shaft, they are formed from rigid material and at certain points in their travel around the bone, they can create a lever action which actually causes a pulling of the soft tissue away from the bone and/or significant spreading of the incision. Further, it would be difficult and impractical to provide a selection of wire passers, each with a curvature diameter to closely match the cross-sectional diameter of each location any given bone, much less provide wire passers with diameters for every bone on which cerclage techniques would be appropriate. The resulting curvature mismatch may either cause the tip of the wire passer to intrude into the surrounding soft tissue at points along its travel, or will require the incision to be spread (or will require a larger initial incision) to permit the tip to closely follow the bone circumference. Also, because of the rigidity of the prior art wire passers, it is not possible to make a device which fully encircles the bone to bring the distal end of the passer completely around to meet the handle portion at the entrance site. Therefore, the incision must be spread, effectively prying the musculature away from the bone, in order for the surgeon to see the eyelet for insertion of the cerclage wire.

As a result of the above-identified deficiencies in the prior art, there remains a need for a wire passer that readily conforms to the bone circumference without excessive stripping of musculature away from the bone, without intrusion into surrounding musculature, and without spreading the incision or requiring a large incision to provide the range of movement necessary to guide a rigid tip around the bone and to visually find the eyelet for insertion of the wire. The wire passer disclosed in the following written description and drawings addresses and overcomes each of these deficiencies.

SUMMARY OF THE INVENTION

The cerclage wire passer disclosed herein overcomes the problems of soft tissue trauma by providing a flexible, retractable tip that readily curves around and conforms to the bone circumference without requiring manipulation of the device to elevate musculature away from the bone, thereby eliminating undue tissue damage.

In an exemplary embodiment the cerclage instrument, or wire passer, comprises a hollow housing having means at its proximal end for gripping in the user's hand to support and control movement of the device. At the distal end of the housing is a tapered tip with an opening therein. Disposed slidably within the housing is an extendable tongue formed from spring metal or similar material that will coil or curl to form a circle when extended outside of the housing. At its distal end, the tongue has an eyelet, notch, or other means for retaining the end of a cerclage wire so that it can be pulled around the bone when the tongue is retracted into the housing. At its proximal end, the tongue is attached to a plunger or slide means within the housing which permits the tongue to be extended from and retracted into the housing. In one embodiment, the plunger extends from the proximal end of the housing and has a hand grip by which the user may control extension and retraction of the tongue by sliding the plunger hand grip relative to the housing. In another embodiment, a thumb slide extends through a channel in the side wall of the housing so that the tongue may be extended and retracted by placing the user's thumb on the slide and moving the slide toward and away the distal end, respectively.

The spring metal of which the tongue is formed is selected to curl to a diameter that closely follows the circumference of the bone to be wired. The distal end of the tongue is polished and rounded across both the width and the thickness of the metal to eliminate sharp edges that might cause tissue injury. While in its retracted state, the tongue is supported by a narrow guide channel within the distal end of the housing which forces it to remain straight and aligned with the end opening so that it can be easily extended when desired.

In an alternate embodiment, the tongue is formed from a pre-coiled steel cable which possesses the mechanical properties described for a spring metal tongue, i.e., the cable curls to form a loop when extended.

The housing is openable, preferably being formed as two halves which are fastened together with screws or other suitable fasteners. The housing may be opened for cleaning of all components and for replacement of the tongue.

BRIEF DESCRIPTION OF THE DRAWINGS

Understanding the present invention will be facilitated by consideration of the following detailed description of preferred embodiments of the present invention taken in conjunction with the accompanying drawings, in which like numerals refer to like parts and in which.

DETAILED DESCRIPTION OF THE PREFERRED EMBODIMENT

Figure 1:
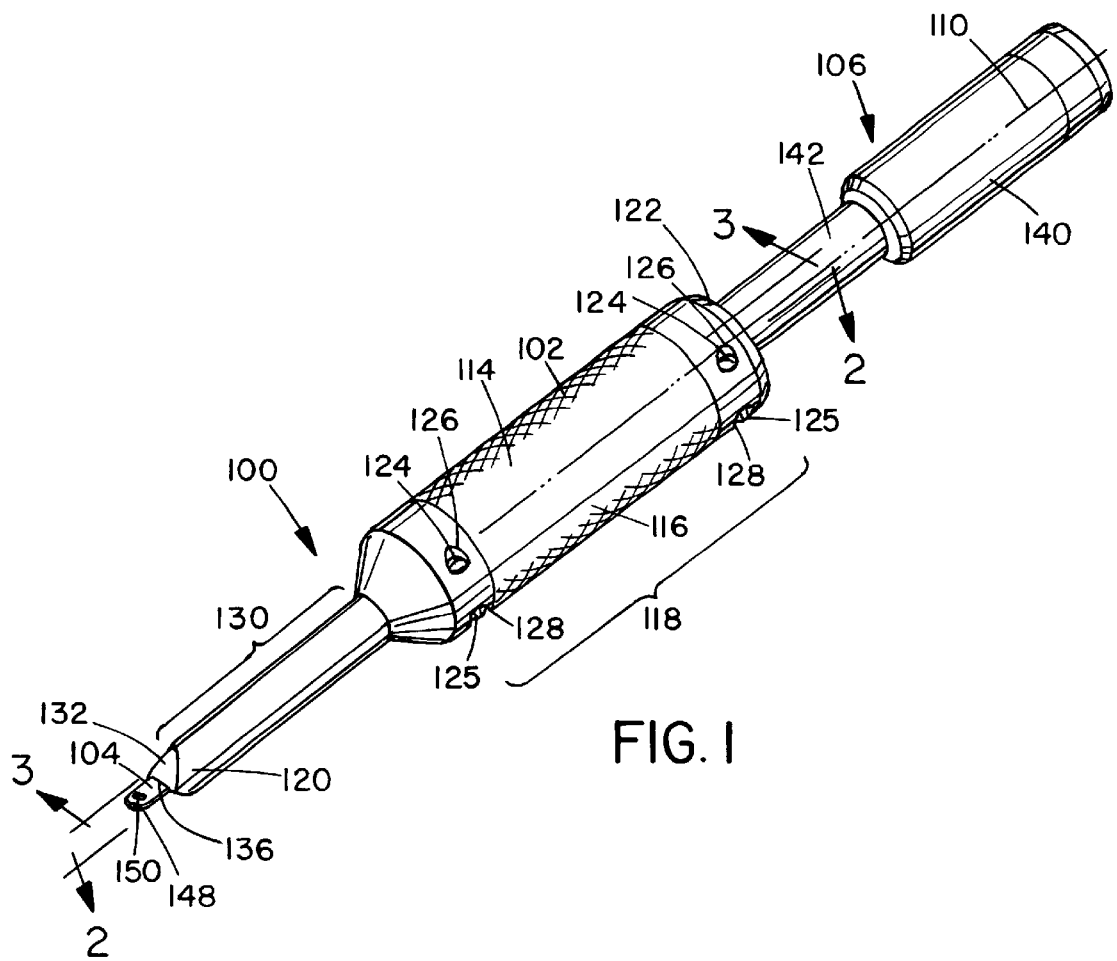
FIG. 1 is a perspective view of a first embodiment of the cerciage instrument.
Figure 2:
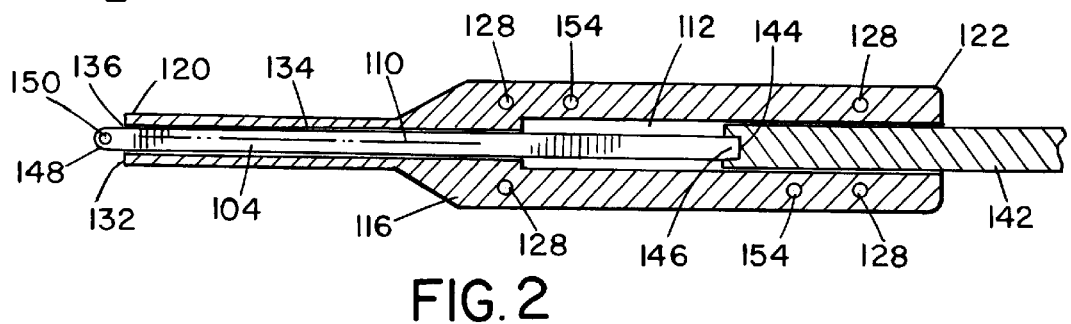
FIG. 2 is a cross-sectional view taken along line 2—2 of FIG. 1.
Figure 3:
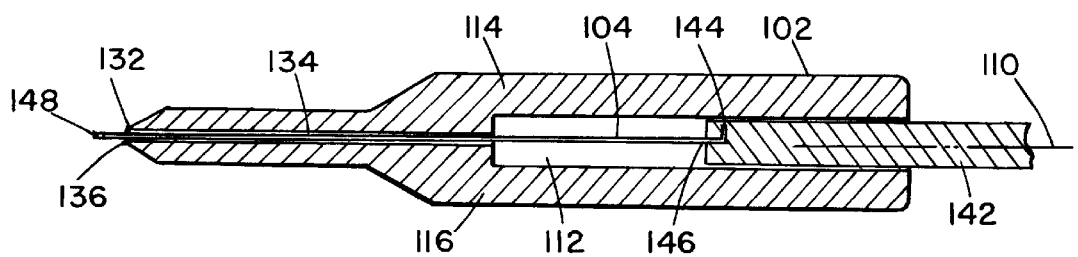
FIG. 3 is a cross-sectional view taken along line 3—3 of FIG. 1.

A first exemplary embodiment of the cerclage wire passer is illustrated in FIGS. 1–3 and is generally designated by reference numeral 100. As shown, wire passer 100 consists of a housing 102, extendable portion 104, and plunger 106 for moving tongue 104 in and out of housing 102.

Housing 102 is a generally cylindrical body with distal end 120 and proximal end 122 lying along axis 110. A cylindrical chamber 112 within housing 102 may be centered on, or slightly offset from, axis 110. The exterior shape of the housing is not critical, however, it should be dimensioned, and is preferably shaped, to comfortably fit within the user's hand, and may include tapering or a bulb near proximal end 122. Exemplary dimensions for the handle portion 11 8 of housing 102 include a diameter of 25.4 mm (1") and a length of 152 mm (6"). The surface of handle portion 118 may be knurled or otherwise finished to enhance the user's grip. The interior, hollow portion of housing 102 has two different sections, a first corresponding to handle portion 118 and a second corresponding to extension 130, the former having a larger volume than the latter.

Housing 102 is formed in two halves—top half 114 and bottom half 116, which are fastened together using screws 124 inserted through bores 126 and 128 in the top and bottom halves, respectively. Bores 126 may be smooth or threaded and are countersunk so that the heads of screws 124 are recessed in the housing. Bores 128 in bottom half 116 may be threaded or may be smooth if machine screws are used in combination with corresponding nuts 125. In the latter case, bores 128 are also countersunk so that nuts 125 are recessed in the housing. Dowel pins (not shown) may be provided in one of the housing halves to mate with corresponding bores 154 (shown in FIG. 2) in the other half to prevent lateral slippage of the halves while the screws are being inserted.

Handle portion 118 tapers to a smaller diameter at its distal end to extension 130. Exemplary dimensions for extension 130 are 63.5 mm (2.5") long and 10.2 mm (0.4") diameter. Extension 130, which retains extendable portion 104, tapers downward from the top at its distal end to tip 132, which has an exemplary thickness of 2.54 mm (0.1"). The taper angle to tip 132 is on the order of 30° C. Channel 134 is formed within extension 130 within which extendable portion 104 is guided into and out of the housing through slotted opening 136 in tip 132. Exemplary dimensions of channel 134 and opening 136 are a height of 0.76 mm (0.030") and a width of 6.35 mm (0.24") for use when extendable portion 104 is in a flattened configuration, which is further described below. As illustrated, channel 134 and opening 136 are formed in bottom half 116 to simplify machining, however, these features may also be formed by machining both the top and bottom halves of housing 102. The dimensions of channel 134 and opening 136 closely fit those of tongue 104 to assure that its travel does not deviate from a straight line extending perpendicular to opening 136.

As shown in FIG. 2, plunger 106 consists of a handle portion 140 and slide portion 142 which fits and slides within chamber 112. At the distal end of slide portion 142 is notch 144 which retains the proximal end 146 of extendable portion 104 without requiring fasteners. Notch 144 is formed using two lengthwise cuts—one parallel to axis 110, i.e., horizontal as shown in FIG. 3, and the other perpendicular to the plane of the first cut, i.e., vertical, forming a right-angle notch which will frictionally retain proximal end 146 of extendable portion 104 when it is bent at approximate right angles and slid sideways into notch 144. Exemplary dimensions for plunger 106 are as follows: handle portion 140: 127 mm (5") long, 19 mm (0.75") diameter; slide portion 142: 129.5 mm (5.1") long, 9.5 mm (0.375") diameter. The first hollow portion of housing 102 corresponds to the volume within which slide portion 142 will move, and, thus, has dimensions which closely fit slide portion 142 while still allowing the parts to slide relative to each other.

Exemplary dimensions for notch 144 are 1.5 mm (0.06") high in the vertical leg and 3.3 mm (0.13") long in the horizontal leg, 0.75 mm (0.03") wide and 6.35 mm (0.25") across. At the distal end of the first hollow portion, the hollow is reduced to the slotted cross-section corresponding to channel 134. The abrupt decrease in cross-section of the hollow area provides a stop to prevent further forward movement of slide portion 142. The exterior surface of handle portion 140 may be knurled or otherwise treated as above for housing 102 for enhanced gripability.

The material of which both the housing 102 and plunger 106 are formed is stainless steel, preferably type 303 or 304 stainless steel, or any metal exhibiting corrosion resistance and which can be sterilized by autoclave, to meet the generally accepted criteria for surgical instruments.

Extending portion, or tongue, 104 can be any resilient material which can be retracted into the housing 102 and which, when extended from the housing, curls to form a generally circular loop. As illustrated in FIGS. 1–3 and 5a–d, extending portion 104 is a narrow flat strip formed from a spring metal, preferably stainless steel such as type 302, which is chemically, thermally and/or mechanically processed to cause the metal to curl when it is not loaded. Other metals, and other materials, such as resilient plastics or polymers, may also used to form tongue 104 as long as they provide the curling capability and resilience required to perform the functions described herein. The thickness of tongue 104 is on the order of 0.74 mm (0.29"), with a width of approximately 5.8 mm (0.23"). As is known in the spring art, the curvature or deflection of spring metal can be selected by the method(s) and degree of surface processing, e.g., lapping, annealing, or shot peening. For the wire passer, the deflection of tongue 104 should be such as to create a curvature that closely follows the circumference of the bone, i.e., to form a circle of approximately the same diameter as the bone. Since tongue 104 is flexible and can be extended and retracted without moving the housing 102 relative to the bone, its curvature need not exactly match the circumference of the bone when tongue 104 is fully extended, but only closely enough that the distal end 148 of tongue 104 remains as close a possible during its travel to the surface of the bone. At the distal end of tongue 104 is an eyelet 150 through which the cerclage wire can be threaded to pull the wire around the bone. Alternatively, or in addition, a small loop or lip can be formed in the distal end 148 to hold an end of the wire as it is pulled around the bone, particularly when cerclage wire with eyes or loops in the ends is used, or where other cerclage devices, such as cables, bands or straps are used. (For purposes of this description, the term "eyelet" is intended to include any hole, loop, notch, or hook which is capable of temporarily holding the end of a cerclage wire or other device to tongue 104 for purposes of passing the cerclage wire or other device around the bone. Similarly, for purposes of this description, the term "cerclage wire" is intended to include wires as well as other devices that are used in cerclage procedures for internal fixation of bone fractures.) The end 148 and side edges of tongue 104 are rounded and polished to eliminate sharp edges which could cause further tissue damage.

The length of tongue 104 should be such that it can fully encircle the bone, allowing distal end 148 to return to the initial starting point when fully extended, so that it is visible without requiring excessive spreading of the incision. This feature makes it possible to complete the procedure using a smaller initial incision with less spreading and less pulling of musculature away from the bone.

Figure 4:
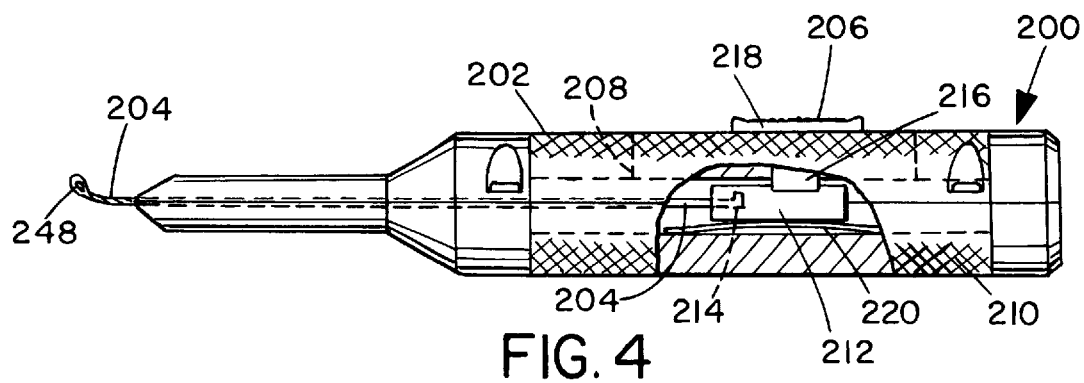
FIG. 4 is side elevational view, partially cut away, showing a second embodiment of the cerclage instrument.

As illustrated in the alternate embodiment of FIG. 4, extendable tongue 204 is formed from a pre-coiled cable, which may be flattened or may have a generally circular cross-section. Here, a circular cross-section twisted wire steel cable is shown, however, other types of wires or cables may be used as long as they possess the quality of curling to form a loop when extended, and further possess the resiliency to be repeatedly extended and retracted while maintaining the ability to curl to form a loop of the appropriate diameter when extended. An exemplary range of diameters for cable used to form tongue 204 is on the order of 2 mm to 4 mm. The ends of the cable should be sufficiently polished to eliminate any sharp edges. As illustrated, eyelet 248 for capturing and holding the cerclage wire as it is pulled around the bone is created by forming a loop at the distal end of tongue 204.

Generally, the guide channel within housing should have a shape and dimensions to conform to the shape and dimensions of the tongue 204 so that the travel during extension and retraction is smooth.

Assembly of the wire passer is such that tongue 104, 204 can be readily replaced to allow for insertion of different "diameter" tongues for use on a wide range of bone sizes. Also, the ability to replace tongue 104,204 assures sterility, especially if materials other than autoclavable stainless steel are used. The fastener-free attachment method for connecting tongue 104,204 to the plunger facilitates rapid replacement of the tongue. Using the example of the embodiment of FIGS. 1–3, access for removing/replacing tongue 104 is obtained by removing screws 124, separating halves 114 and 116, and sliding the proximal end 146 parallel to the width of notch 144 to separate tongue 104 from plunger 106.

Referring again to the second embodiment of the wire passer shown in FIG. 4 (generally designated as 200), the device has the same basic features and function as the first embodiment, but substitutes a thumb slide 206 on the exterior of housing 202 which is connected to tongue 204 through slide channel 208. The dimensions of housing 202 can be generally the same as the dimensions for the first embodiment, however, the absence of the plunger makes the overall device significantly shorter. Therefore, it may be desirable to lengthen the handle portion 210 of housing 202 for easier handling. Further, since the tongue 204 is generally rounded, the guide channels within housing 202 should be shaped and dimensioned accordingly.

As shown, tongue 204 is attached to internal slide 212 by means similar to that for the first embodiment—by a notch in the distal end 214 of slide 212 to accept the bent proximal end 216 of tongue 204, or may be attached by placing dowel pins in the distal end 214 to mate with holes through the proximal end of tongue 204. Other appropriate means for temporary attachment of the tongue 204 to the slide 212 will be apparent to those familiar with mechanical fastening techniques. (This is also true for the first embodiment.) Slide extension 216 extends through slide channel 208 in the sidewall of handle portion 210 to connect internal slide 212 to external slide 218. External slide 218 will be generally flattened, but may have a depression for placement of the user's thumb, and may have ridges (as shown) or knurling to enhance friction between the surface of slide 218 and the user's thumb. Bias spring 220 may be located within the housing below internal slide 212 to provide a slight outward force to prevent movement of the slide except when external slide 218 is pressed downward by the user. Bias spring 220 may be a leaf spring or flat spring having a length corresponding to the length of travel of the thumb slide 206.

It should be noted that the device as illustrated in the figures, including the embodiment of FIG. 4, is not drawn to scale or to proper proportion. Generally, the length of slide channel 208 should correspond to the desired extension of tongue 204, i.e., a direct one-to-one transfer of movement, however, as is known to those in the mechanical arts, means can be provided for increasing the ratio of movement of the tongue 204 for a given movement of the thumb slide 206. The reduction of the range of movement of the thumb slide 206 would enhance the ability to perform the placement, extension and retraction of the tongue 204 using only one hand to hold the instrument, freeing the other hand for manipulation of the tissue around the bone and for holding the end of the cerclage wire as the other end is guided around the bone.

Figure 5A:
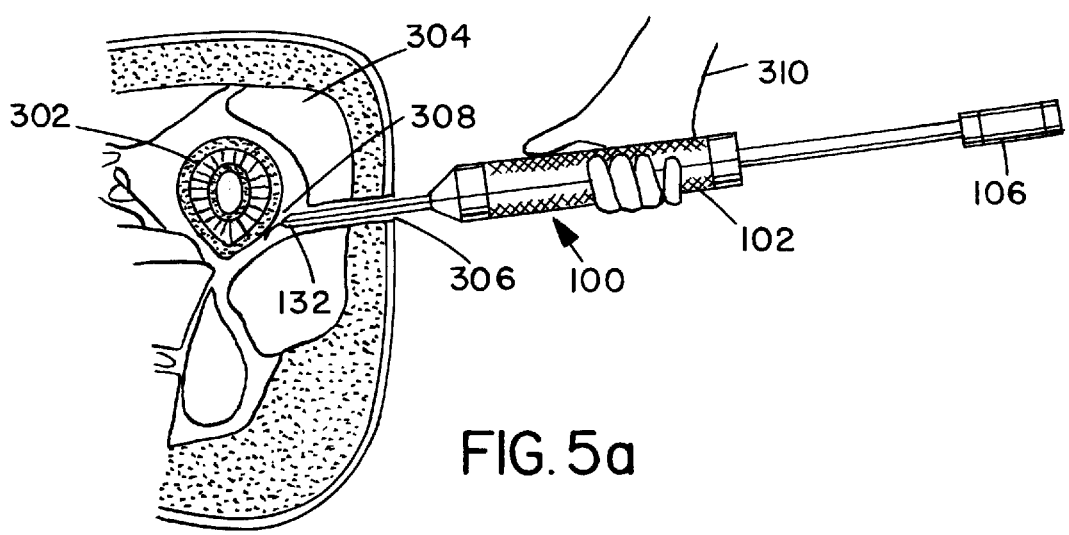
FIGS. 5a–5d are partial sectional views through a long bone and the surrounding soft tissue illustrating the initial placement of the device (FIG. 5a), partial extension of the flexible tongue (FIG. 5b), full extension of the flexible tongue (FIG. 5c), and retraction of the flexible tongue to pull the cerclage wire around the bone (FIG. 5d).
Figure 5B:
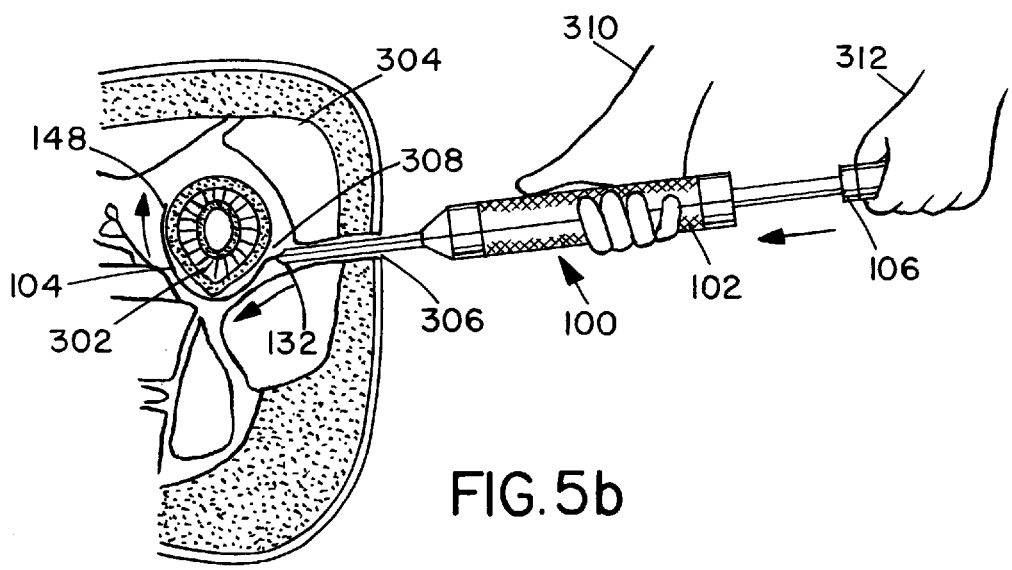
Figure 5C:
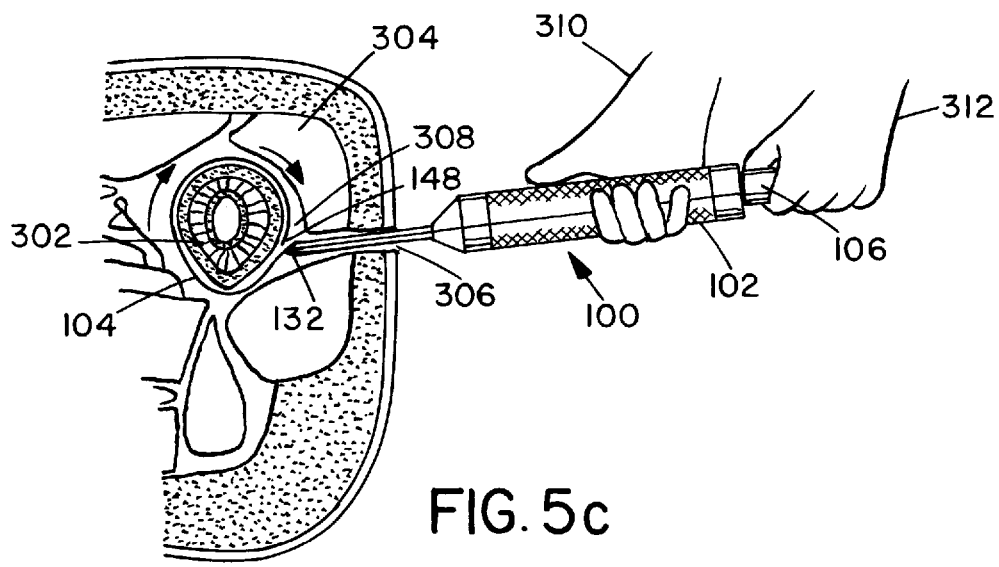
Figure 5D:
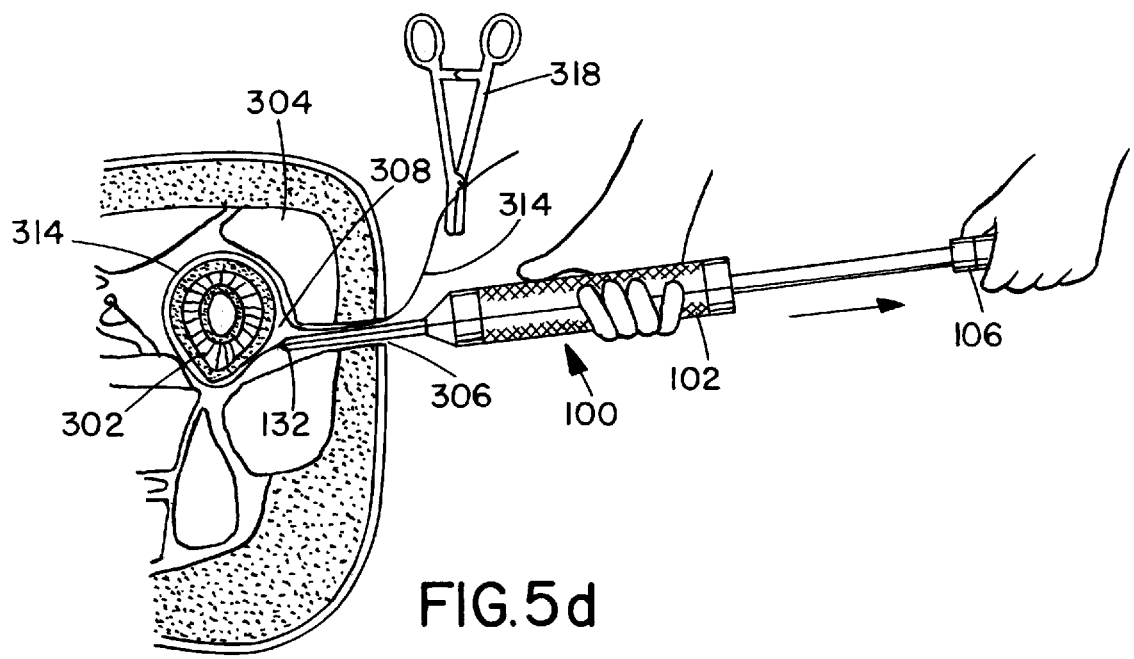

FIGS. 5a–5d illustrate the method of using the wire passer of the first embodiment. A cross-section of the shaft of a long bone 302 and the surrounding soft tissue 304 is shown with incision 306. In FIG. 5a, with tongue 104 retracted, the surgeon's hand 310 holds the device 100 to place the tip 132 at starting point 308 so that it is positioned to feed tongue 104 tangent to the bone. As illustrated, it can be seen that little spreading of the incision is required to position tip 132 at starting point 308. As shown in FIG. 5b, the surgeon's other hand 312 depresses plunger 106, causing tongue 104 to be extended and gradually releasing the tongue from the force inside the housing 102 that had been maintaining it in a straightened configuration. As tongue 104 is extended it curls, causing distal end 148 of tongue 104 to follow the circumference of the bone 302. Once fully extended, as in FIG. 5c, a circle is formed and distal end 148 of tongue 104 has returned to starting point 308 and should be readily visible to the surgeon by minimal spreading of the incision 306 so that one end of cerclage wire 314 can be threaded through the eyelet (not visible in the figure.) Assuring that the free end of wire 314 remains accessible, shown here secured by forceps 318, plunger 106 is pulled away from housing 102 causing tongue 104 to be retracted into housing 102, pulling with it the attached end of cerclage wire 314, as shown in FIG. 5d. The natural curvature of tongue 104 again causes its distal end 148 to closely follow the circumference of the bone 302 as it is retracted, with no intrusion into the surrounding tissue 304. Once the tongue 104 is fully retracted, the instrument 100 is pulled away from the incision to permit access to both ends of the cerclage wire 314 so that they can be twisted together. During this procedure, no rotation of the wire passer 100 is required to work the tip around the circumference of the bone, nor is there any need to change the tangential angle of the wire passer 100 with respect to the bone, both of which motions are required for use of prior art wire passers. Therefore, apart from the incision to provide access to the bone and to the wire after it has been passed around the bone, no forces are applied which might increase trauma to the surrounding tissue 304.

It will be apparent to those skilled in the art that various modifications and variations can be made in the device and method of the present invention without departing from the spirit or scope of the invention. Thus, it is intended that the present invention cover the modification and variations of this invention provided they come within the scope of the appended claims and their equivalence.

We claim:

1. A wire passer for placement of a cerclage wire for internal fixation of a bone, the wire passer comprising:
    a housing having a proximal portion and a distal portion, with a handle means at the proximal portion of the housing and a tip at an end of the distal portion of the housing, the housing being substantially hollow and having a tip opening in the tip;
    an extendable tongue formed from a generally flattened strip of resilient material which, when unloaded, curls to substantially form a loop of a pre-determined diameter generally corresponding to a bone diameter of the bone the tongue having a distal end and a proximal end and being slidably disposed within the distal portion of the housing so that the tongue can be extended through the tip opening;
    an eyelet means formed in the distal end of the tongue for retaining an end of the cerclage wire; and
    a slide means attached to the proximal end of the tongue and being longitudinally slidably disposed within the proximal portion of the housing so that the slide means can move longitudinally within the housing to extend and retract the tongue through the tip opening.

2. A wire passer as in claim 1, wherein the slide means is a plunger.

3. A wire passer as in claim 1, wherein the tongue is formed from a strip of flat spring metal.

4. A wire passer as in claim 1, wherein the tongue is formed from a pre-coiled steel cable.

5. A wire passer as in claim 1, wherein the housing comprises two halves which are openable to permit access to the proximal end of the tongue and the slide means.

6. A wire passer as in claim 1, wherein the housing and the slide means are each formed from stainless steel of a type suitable for surgical instruments.

7. A wire passer as in claim 1, wherein the tongue is formed from stainless steel.

8. A wire passer as in claim 1, wherein the distal portion of the housing has a channel formed therein for retaining the tongue in a substantially flattened condition when the tongue is retracted within the housing.

9. A wire passer as in claim 1, wherein the tongue is removably attached to the slide means.

10. A wire passer as in claim 1, wherein the slide means is a thumb slide extending through a slide channel within the housing.

11. A cerclage instrument for positioning a cerclage wire for fixation of a fracture in a bone, the cerclage instrument comprising:
    a housing having a handle portion and an extension portion, the handle portion having a hollow portion therein and the extension having a hollow channel therein in communication with the hollow portion, and having a tip end with a tip opening in communication with the hollow channel;
    a slide means slidably disposed within the hollow portion for sliding longitudinally within the hollow portion, the slide means having means for manually controlling its sliding and having an attachment means;
    a tongue formed from a generally flattened strip of resilient material which curls when unloaded to substantially form a circle, the tongue having a distal end with an eyelet formed therein and a proximal end with means for mating with the attachment means of the slide means wherein longitudinal movement of the slide means within the housing causes the tongue to move with respect to the tip opening so that the tongue can be extended from and retracted into the hollow channel through the tip opening, wherein the eyelet is adapted for retaining an end of the cerclage wire so that the cerclage wire can be pulled by retracting the tongue.

12. A cerclage instrument as in claim 11, wherein the slide means is a plunger.

13. A cerclage instrument as in claim 11, wherein the slide means is a thumb slide extending through a slide channel within the housing.

14. A cerclage instrument as in claim 11, wherein the housing comprises two halves which are openable to permit access to the proximal end of the tongue and the slide means.

15. A cerclage instrument as in claim 11, wherein the housing and the slide means are each formed from stainless steel of a type suitable for surgical instruments.

16. A cerclage instrument as in claim 11, wherein the tongue is formed from spring metal.

17. A cerclage instrument as in claim 11, wherein the tongue is formed from pre-coiled steel cable.

18. A method for passing cerclage wire around a bone for internal fixation of a bone fracture, the method comprising:
    providing a cerclage instrument having a hollow housing with a tapered tip having a tip opening, and a slide means attached to an extendable tongue formed from a generally flattened strip of resilient material which curls to form a circle when unloaded and having an eyelet near a tongue end for receiving an end of the cerclage wire, the slide means and tongue moving slidably within the hollow housing to extend and retract the tongue through the tip opening;

supporting the hollow housing to position the tapered tip of the cerclage instrument adjacent the bone at a tangent to the circumference of the bone with the tongue of the cerclage instrument retracted;

maintaining the position of the hollow housing and sliding the slide means relative to the hollow housing to extend the tongue, wherein the tongue end follows the circumference of the bone so that, when fully extended, the tongue substantially encircles the bone;

threading a first end of the cerclage wire through the eyelet near the tongue end so that the wire can be pulled by the tongue;

maintaining the position of the hollow housing and sliding the slide means with respect to the hollow housing to retract the tongue while holding a second end of the cerclage wire so that the cerclage wire is passed around the bone; and removing the first end of the wire from the eyelet.

19. The method of claim 18, wherein the step of providing a cerclage instrument includes forming the hollow housing and slide means from stainless steel of a type suitable for surgical instruments.

20. The method of claim 18, wherein the step of providing a cerciage instrument includes forming the tongue from a pre-coiled steel cable.

* * * * *

UNITED STATES PATENT AND TRADEMARK OFFICE
CERTIFICATE OF CORRECTION

PATENT NO. : 5,810,832
DATED : Sept. 22, 1998
INVENTOR(S) : James Blasingame, *et al.*

It is certified that error appears in the above-identified patent and that said Letters Patent is hereby corrected as shown below:

In column 1, line 16, please delete "Cerciage" and substitute --Cerclage-- therefor.

In column 4, line 15, please delete "C".

In column 4, line 34, please delete "30".

Signed and Sealed this

Thirty-first Day of August, 1999

Attest:

Attesting Officer

Q. TODD DICKINSON

Acting Commissioner of Patents and Trademarks